United States Patent [19]

Benedict et al.

[11] Patent Number: 5,583,122
[45] Date of Patent: Dec. 10, 1996

[54] PHARMACEUTICAL COMPOSITIONS CONTAINING GEMINAL DIPHOSPHONATES

[75] Inventors: James J. Benedict, Norwich, N.Y.; Christopher M. Perkins, Cincinnati, Ohio

[73] Assignee: The Procter & Gamble Company, Cincinnati, Ohio

[21] Appl. No.: 806,155

[22] Filed: Dec. 6, 1985

Related U.S. Application Data

[63] Continuation-in-part of Ser. No. 684,543, Dec. 21, 1984, abandoned.

[51] Int. Cl.$^6$ .................. C07F 9/38; C07F 9/58; A61K 31/675
[52] U.S. Cl. .................. 514/89; 546/22
[58] Field of Search .................. 514/89; 546/23, 546/22

[56] References Cited

U.S. PATENT DOCUMENTS

| | | | |
|---|---|---|---|
| 3,553,314 | 1/1971 | Francis | 424/49 |
| 3,683,080 | 8/1972 | Francis | 514/107 |
| 3,846,420 | 11/1974 | Wollmann et al. | 544/157 |
| 3,941,772 | 3/1976 | Ploger et al. | 546/6 |
| 3,957,160 | 5/1976 | Ploger et al. | 210/58 |
| 3,960,888 | 6/1976 | Ploger et al. | 548/412 |
| 3,979,385 | 9/1976 | Wollmann et al. | 544/157 |
| 3,988,443 | 10/1976 | Ploger et al. | 514/79 |
| 4,034,086 | 7/1977 | Ploger et al. | 514/91 |
| 4,100,167 | 7/1978 | Selvarajan et al. | 260/296 R |
| 4,117,090 | 9/1978 | Ploger | 423/268 |
| 4,134,969 | 1/1979 | Schmidt-Dunker | 424/49 |
| 4,239,695 | 12/1980 | Chai et al. | 260/502.5 |
| 4,267,108 | 5/1981 | Blum et al. | 260/326.61 |
| 4,304,734 | 12/1981 | Jary et al. | 562/13 |
| 4,407,761 | 10/1983 | Blum et al. | 562/13 |
| 4,447,255 | 5/1984 | Suzuki et al. | 71/86 |
| 4,447,256 | 5/1984 | Suzuki et al. | 71/86 |
| 4,473,560 | 9/1984 | Biere et al. | 514/95 |
| 4,503,049 | 3/1985 | Biere et al. | 514/80 |
| 4,608,368 | 8/1986 | Blum et al. | 514/107 |
| 4,621,077 | 11/1986 | Rosini et al. | 514/108 |
| 4,687,767 | 8/1987 | Bosies et al. | 514/89 |
| 4,687,768 | 8/1987 | Benedict et al. | 514/102 |
| 4,696,920 | 9/1987 | Bentzen et al. | 514/89 |
| 4,719,203 | 1/1988 | Bosies et al. | 514/108 |
| 4,777,163 | 10/1988 | Bosies et al. | 514/80 |

FOREIGN PATENT DOCUMENTS

| | | |
|---|---|---|
| 88359 | 9/1983 | European Pat. Off. . |
| 100718 | 2/1984 | European Pat. Off. . |
| 0170228 | 2/1986 | European Pat. Off. . |
| 2343476 | 4/1975 | Germany . |
| 2513966 | 10/1976 | Germany . |
| 2541981 | 3/1977 | Germany . |
| 53-59674 | 5/1978 | Japan . |
| 54-135724 | 10/1979 | Japan . |
| 55-98193 | 7/1980 | Japan . |
| 2004888 | 4/1979 | United Kingdom . |

OTHER PUBLICATIONS

C.A. vol. 93(1980) 93: 232711f, Nissan Chem. Ind.
C.A. vol.93(1980) 93: 199,239h, Nissan Chem. Ind.
Worms Q.A. vol. 77 (1972) 130478N.
C.A. vol. 94(1981) 94:11638f Nissan Chem. Ind.
Francis & Martodam, "Chemical, Biochemical, & Medicinal Properties of the Diphosphonates", in *The Role of Phosphonates in Living Systems* (CRC Press; Hilderbrand editor), pp. 55–96 (1983).
Unterspann, "Experimental Examinations on the Suitability of Organoaminomethane–bis–Phosphonic Acids for Bone-Scintigraphy by Means of Tc–99m in Animals", Eur. J. Nucl. Med., vol. 1, pp. 151–154 (1976).
Sologub et al., "Synthesis and Intramolecular Electronic Interactions in Molecules of Tetrachloropyridyl–4–carbonimidoyl Dichloride and Its Derivatives", Khim. Geterotsikl. Soedin, 1983, (6), pp. 798–800; abstract attached Chem. Abs. 99:122,246z.
Maier, "Organophosphorous Compounds. Part 75", Phosphorus Sulfur, vol. 11 (3), pp. 311–22 (1981): abstract attached Chem. Abst. 96:52398n, plus article.
Ploeger et al., "Preparation of 1–Aminoalkylidene Diphosphonic Acids", *Z. Anorg. Allg. Chem.*, vol. 389 (2), pp. 119–28 (1972); (original and English translation attached).
Grapov et al., "Reaction of Ethyl–N–2–pyridylimidoformate with Dialkylphosphites" *Zh. Obshch. Khim.*, vol. 57 (7), pp. 1655–1657 (1980); abstract attached Chem. Abst. 93:220, 855t.
Bandurina et al., "Synthesis of Some Aminophosphonic Acids and Their Antineoplastic Activity", *Khim.–Farm. Zh.*, vol. 12 (11), pp. 35–37 (1978); Chem. Abst. 90:115,081c.

Primary Examiner—Alan L. Rotman
Attorney, Agent, or Firm—K. W. Zerby; David L. Suter

[57] ABSTRACT

Pharmaceutical compositions, useful for treating abnormal calcium and phosphate metabolism, which contain geminal-diphosphonic acid compounds; and a method of treating diseases characterized by abnormal calcium and phosphate metabolism utilizing these pharmaceutical compositions.

23 Claims, No Drawings

PHARMACEUTICAL COMPOSITIONS CONTAINING GEMINAL DIPHOSPHONATES

CROSS REFERENCE TO RELATED APPLICATION

This application is a Continuation-in-Part of prior application Ser. No. 684,543, filed Dec. 21, 1984, now abandoned.

TECHNICAL FIELD

This invention relates to pharmaceutical compositions containing compounds which are useful in treating or preventing diseases characterized by abnormal calcium and phosphate metabolism, in particular those which are characterized by abnormal bone metabolism. This invention further relates to a method of treating or preventing diseases characterized by abnormal calcium and phosphate metabolism using pharmaceutical compositions of the present invention.

BACKGROUND OF THE INVENTION

A number of pathological conditions which can afflict warm-blooded animals involve abnormal calcium and phosphate metabolism. Such conditions may be divided into two broad categories.

1. Conditions which are characterized by anomalous mobilization of calcium and phosphate leading to general or specific bone loss or excessively high calcium and phosphate levels in the fluids of the body. Such conditions are sometimes referred to herein as pathological hard tissue demineralizations.

2. Conditions which cause or result from deposition of calcium and phosphate anomalously in the body. These conditions are sometimes referred to herein as pathological calcifications.

The first category includes osteoporosis, a condition in which bone hard tissue is lost disproportionately to the development of new hard tissue. Marrow and bone spaces become larger, fibrous binding decreases, and compact bone becomes fragile. Osteoporosis can be subclassified as menopausal, senile, drug induced (e.g., adrenocorticoid, as can occur in steroid therapy), disease induced (e.g., arthritic and tumor), etc., however, the manifestations are essentially the same. Another condition in the first category is Paget's disease (osteitis deformans). In this disease, dissolution of normal bone occurs which is then haphazardly replaced by soft, poorly mineralized tissue such that the bone becomes deformed from pressures of weight bearing, particularly in the tibia and femur. Hyperparathyroidism, hypercalcemia of malignancy, and osteolytic bone metastases are conditions also included in the first category.

The second category, involving conditions manifested by anomalous calcium and phosphate deposition, includes myositis ossificans progressiva, calcinosis universalis, and such afflictions as arthritis, neuritis, bursitis, tendonitis and other inflammatory conditions which predispose involved tissue to deposition of calcium phosphates.

Polyphosphonic acids and their pharmaceutically-acceptable salts have been proposed for use in the treatment and prophylaxis of such conditions. In particular diphosphonates, like ethane-1-hydroxy-1,1-diphosphonic acid (EHDP), propane-3-amino-1-hydroxy-1,1-diphosphonic acid (APD), and dichloromethane diphosphonic acid ($Cl_2MDP$) have been the subject of considerable research efforts in this area. Paget's disease and heterotopic ossification are currently successfully treated with EHDP. The diphosphonates tend to inhibit the resorption of bone tissue, which is beneficial to patients suffering from excessive bone loss. However, EHDP, APD and many other prior art diphosphonates have the propensity of inhibiting bone mineralization when administered at high dosage levels.

It is believed that mineralization inhibition is predominantly a mass related physico-chemical effect, whereas resorption inhibition results from a biological interaction with the cells. It is therefore desirable to develop more biologically potent diphosphonate compounds that can be administered at low dosage levels which cause little or no mineralization inhibition, thereby resulting in a wider margin of safety. Low dosage levels are also desirable to avoid the gastro-intestinal discomfort (like diarrhea) sometimes associated with oral administration of large quantities of diphosphonates.

It is therefore an object of this invention to provide high potency compositions for the treatment and prophylaxis of abnormal calcium and phosphate metabolism. It is a still further object of this invention to provide an improved method for treating diseases characterized by abnormal calcium and phosphate metabolism.

BACKGROUND ART

U.S. Pat. No. 3,683,080, issued Aug. 8, 1972, to Francis, discloses compositions comprising polyphosphonates, in particular diphosphonates, and their use in inhibiting anomalous deposition and mobilization of calcium phosphate in animal tissue.

Japanese Patent 80-98,193, issued Jul. 25, 1980, to Nissan Kygaku Kagyo K.K. discloses pyridyl ethane diphosphonic acid, S-(pyridyl)-thiomethane diphosphonic acid, and the derivatives with halogen or alkyl group substitution on the pyridyl ring. These compounds are used as post-emergence herbicides.

Japanese Patent 80-98,105, issued Jul. 25, 1980, to Nissan Chemical Industries, discloses N-(3-pyridyl)-aminomethane diphosphonic acid, and the derivatives with halogen or alkyl group substitution on the pyridyl ring, for use as herbicides. Various N-(pyridyl)-aminomethane diphosphonates are also disclosed in West German Patent 2,831,578, issued Feb. 1, 1979 to Fumio, for use as herbicides.

European Patent Application 100,718 (Sanofi SA), published Feb. 15, 1984, discloses various alkyl diphosphonates which are -substituted by a sulfide attached to a 5- or 6-membered nitrogen- or sulfur-containing heterocycle. These compounds are used as anti-inflammatory and anti-rheumatic drugs.

British Patent Application 2,004,888, published Apr. 11, 1979, discloses N-(3-methyl-2-picolyl)-aminomethane and related compounds for use in herbicidal compositions.

W. Ploger et al., *Z. Anorg. Allg. Chem.*, 389, 119 (1972), discloses the synthesis of N-(4-pyridyl)-aminomethane diphosphonic acid. No properties or utility of the compound are disclosed.

SUMMARY OF THE INVENTION

The present invention relates to pharmaceutical compositions comprising:

(a) from about 0.001 mg P to about 600 mg P of a geminal diphosphonic acid compound, or its pharmaceutically-acceptable salt or ester, in which the diphosphonic acid-containing carbon is linked directly, or via a chain of length from 1 to about 5 atoms, to a 6-membered aromatic ring containing one or more nitrogen atoms with the parts of said compound being comprised as follows:

said ring may be unsubstituted or substituted with one or more substituents selected from the group consisting of substituted and unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof;

said linking chain may be all carbon atoms, a nitrogen atom or nitrogen-containing chain, an oxygen atom or oxygen-containing chain, or a selenium atom or selenium-containing chain, with said chain being unsubstituted or substituted on the nitrogen and/or carbon atoms, independently, with one or more substituted or unsubstituted alkyl (saturated or unsaturated) having from 1 to about 4 carbon atoms, and said nitrogen atom also may be substituted with an acyl group;

said diphosphonate-containing carbon may be unsubstituted or substituted with substituted or unsubstituted alkyl (saturated or unsaturated) having from 1 to about 6 carbon atoms, substituted or unsubstituted aryl, substituted or unsubstituted benzyl, amino, substituted amino, amido, hydroxy, alkoxy, halogen or carboxylate, except where said diphosphonate-containing carbon is directly bonded to a nitrogen, selenium, or oxygen atom in the linking chain, then the substituents may be substituted or unsubstituted alkyl (saturated or unsaturated) having from 1 to about 6 carbon atoms, substituted or unsubstituted aryl, or substituted or unsubstituted benzyl; and (b) a pharmaceutical carrier.

The invention further encompasses a method of treating diseases characterized by abnormal calcium and phosphate metabolism, comprising administering to a human or animal in need of such treatment a safe and effective amount of a diphosphonic acid-containing composition of the present invention.

DETAILED DESCRIPTION OF THE INVENTION

This invention relates to pharmaceutical compositions, preferably in unit dosage form, comprising a pharmaceutical carrier and a safe and effective amount of geminal diphosphonic acid compounds, or their pharmaceutically-acceptable salts and esters, in which the diphosphonic acid-containing carbon is linked to a 6 membered aromatic ring containing one or more nitrogen atoms. Preferred rings are pyridine, pyridazine, pyrimidine, and pyrazine. Most preferred are pyrimidine, and especially pyridine. The rings may be unsubstituted or substituted with one or more substituents selected from the group consisting of substituted and unsubstituted alkyl (saturated or unsaturated) having from 1 to about 6 carbon atoms, substituted and unsubstituted aryl (e.g., phenyl and naphthyl), substituted and unsubstituted benzyl, hydroxy, halogen, carbonyl (e.g., —CHO and —COCH$_3$), alkoxy (e.g., methoxy and ethoxy), nitro, amido (e.g., —NHCOCH$_3$), amino, substituted amino (e.g., dimethylamino, methylamino, and diethylamino), carboxylate (e.g., —OCOCH$_3$), and combinations thereof. The rings may be fused with other rings, e.g., benzene fused with pyridine (e.g., quinoline), and cyclohexane fused with pyridine (e.g., 5,6,7,8-tetrahydroquinoline). Additional substituents could be substituted or unsubstituted sulfide, sulfoxide, sulfate, or sulfone.

The linkage from the diphosphonic acid-containing carbon to the ring may be direct through a single bond, or by a chain of length of from 1 to about 5 atoms. The chain may be all carbon atoms, a nitrogen atom or nitrogen-containing chain, an oxygen atom or oxygen-containing chain, or a selenium atom or selenium-containing chain. The carbon and nitrogen atoms in the chains may, independently, be unsubstituted or substituted with one (or one or two in the case of carbon atoms) substituted or unsubstituted alkyl (saturated or unsaturated) having from 1 to about 4 carbon atoms (methyl and ethyl being preferred). The nitrogen atoms in the chains may also be substituted with an acyl group (e.g., —COCH$_3$). Unsubstituted carbon and nitrogen atoms in the chain are preferred. Also preferred are chains one atom in length, i.e., —CH$_2$—, —NH—, and —O—.

The carbon atom which has the phosphonate groups attached to it may be unsubstituted (i.e., a hydrogen atom), or substituted with amino, substituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl. For the compounds in which the phosphonate-containing carbon is linked to the ring via an oxygen, selenium, or nitrogen-containing chain, and that oxygen, selenium, or nitrogen atom is bonded directly to the phosphonate containing carbon, then the substituent on the phosphonate-containing carbon may be substituted or unsubstituted alkyl (saturated or unsaturated) having from 1 to about 6 carbon atoms, substituted or unsubstituted aryl, or substituted or unsubstituted benzyl.

Thus, diphosphonic acid compounds to be included in the pharmaceutical compositions of the present invention have the structure:

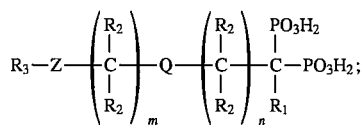

wherein Q is oxygen, —NR$_4$—, selenium, or a single bond, preferred being oxygen, —NR$_4$—, or a single bond; m+n is an integer from 0 to about 5, with m+n=0 or 1 preferred for Q being oxygen, selenium, or —NR$_4$—, and m+n=1 or 2 preferred otherwise; Z is a ring selected from the group consisting of pyridine, pyridazine, pyrimidine, and pyrazine, with preferred being pyrimidine, and especially pyridine; R$_1$ is hydrogen, substituted or unsubstituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl, except that when n=0 and Q is oxygen, selenium, or —NR$_4$— then R$_1$ is hydrogen, substituted or unsubstituted alkyl (saturated or unsaturated) having from 1 to about 6 carbon atoms, substituted or unsubstituted aryl, or substituted or unsubstituted benzyl, with R$_1$ being hydrogen, chloro, amino, methyl, or hydroxy preferred; each R$_2$ is, independently, hydrogen, or substituted or unsubstituted alkyl (saturated or unsaturated) having from 1 to about 4 carbon atoms, with R$_2$ being hydrogen preferred; R$_3$ is one or more substituents selected from the group consisting of hydrogen, substituted or unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof, with preferred being hydrogen, methyl, amino, chloro, methoxy, nitro, hydroxy and combinations thereof; $R_4$ is hydrogen, substituted or unsubstituted alkyl (saturated or unsaturated) having from 1 to about 4 carbon atoms, or acyl (i.e., the amide of the nitrogen), with preferred being hydrogen, methyl, or ethyl; and pharmaceutically-acceptable salts and esters of these compounds. Finally, for any of the $R_1$, $R_2$, $R_3$, or $R_4$ substituents which are themselves substituted, the substitution on these substituents may be any one or more of the above substituents, preferred being methyl, ethyl, amino, chloro, nitro, methoxy, hydroxy, acetamido, and acetate.

More specifically, the diphosphonic acid compounds, and their pharmaceutically-acceptable salts and esters, to be included in the pharmaceutical compositions of the present invention are of the structure:

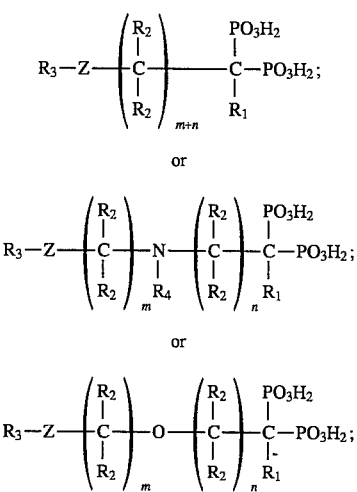

wherein m+n, Z, $R_1$, $R_2$, $R_3$, and $R_4$ are as described above.

Generally preferred diphosphonic acid compounds, and their pharmaceutically acceptable salts and esters, to be included in the pharmaceutical compositions of the present invention are of the structure:

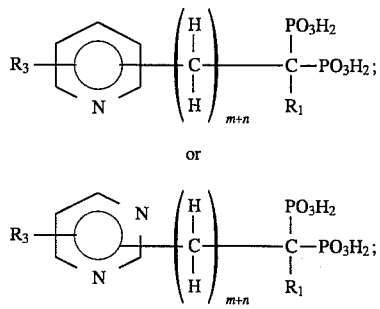

wherein for both structures above m+n=1 or 2; $R_1$ is hydrogen, chloro, amino, or hydroxy; $R_3$ is one or more substituents selected from the group consisting of hydrogen, methyl, amino, chloro, nitro, methoxy, hydroxy, and combinations thereof; or

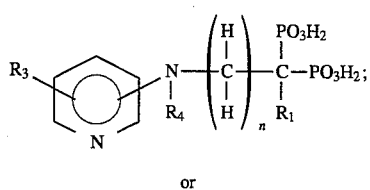

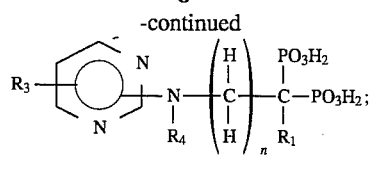

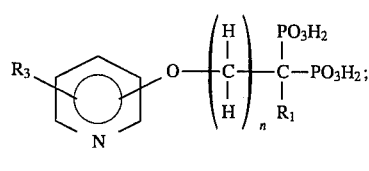

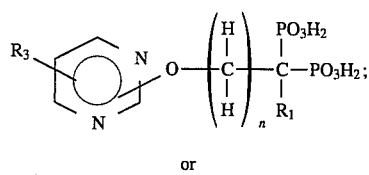

wherein for the four preceding structures n=0 or 1; $R_1$ is hydrogen, chloro, amino, or hydroxy when n=1, and $R_1$ is hydrogen when n=0; $R_3$ is one or more substituents selected from the group consisting of hydrogen, methyl, amino, chloro, methoxy, nitro, hydroxy, and combinations thereof; and $R_4$ is hydrogen, methyl, or ethyl.

Specific examples of compounds which may be utilized in compositions of the present invention include;
N-(2-pyridyl)-aminomethane diphosphonic acid;
N-(2-(5-amino)-pyridyl)-aminomethane diphosphonic acid;
N-(2-(5-chloro)-pyridyl)-aminomethane diphosphonic acid;
N-(2-(5-nitro)-pyridyl)-aminomethane diphosphonic acid;
N-(2-(3,5-dichloro)-pyridyl)-aminomethane diphosphonic acid;
N-(4-pyridyl)-N-ethyl-aminomethane diphosphonic acid;
N-(2-(3-picolyl))-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-(4,6-lutidine))-aminomethane diphosphonic acid;
N-(2-pyrimidyl)-aminomethane diphosphonic acid;
N-(4-(2,6-dimethyl)-pyrimidyl)-aminomethane diphosphonic acid;
N-(2-(4,6-dihydroxy)-pyrimidyl)-aminomethane diphosphonic acid;
N-(2-(5-methoxy)-pyridyl)-aminomethane diphosphonic acid;
N-(2-pyridyl)-2-aminoethane-1,1-diphosphonic acid;
N-(2-(3-picolyl))-2-aminoethane-1,1-diphosphonic acid;
N-(3-pyridyl)-2-amino-1-chloroethane-1,1-diphosphonic acid;
N-(2-(4-picolyl))-2-amino-1-hydroxy-ethane-1,1-diphosphonic acid;
(2-pyridyl)-methane diphosphonic acid;
(3-pyridyl)-aminomethane diphosphonic acid;
(2-pyridyl)-chloromethane diphosphonic acid;
(4-pyridyl)-hydroxymethane diphosphonic acid;
2-(2-pyridyl)-ethane-1,1-diphosphonic acid;
2-(3-pyridyl)-ethane-1,1-diphosphonic acid;
2-(4-pyridyl)-ethane-1,1-diphosphonic acid;
2-(2-pyridyl)-1-amino-ethane-1,1-diphosphonic acid;
2-(2-pyrimidyl)-1-hydroxy-ethane-1,1-diphosphonic acid;
2-(2-(3-picolyl))-1-chloro-ethane-1,1-diphosphonic acid;
2-(2-(4-methoxy)-pyridyl)-ethane-1,1-diphosphonic acid;
1-(2-pyridyl)-propane-2,2-diphosphonic acid;

2-(2-pyridyl)-1-chloro-ethane-1,1-diphosphonic acid;
2-(2-pyridyl)-1-hydroxy-ethane-1,1-diphosphonic acid;
2-(3-pyridyl)-1-hydroxy-ethane-1,1-diphosphonic acid;
2-(4-pyridyl)-1-hydroxy-ethane-1,1-diphosphonic acid;
3-(3-pyridyl)-1-hydroxy-propane-1,1-diphosphonic acid;
O-(2-pyridyl)-2-oxa-ethane-1,1-diphosphonic acid;
O-(2-pyridyl)-oxamethane diphosphonic acid;
O-(2-pyrimidyl)-oxamethane diphosphonic acid;
O-(2-(4-amino)-pyridyl)-oxamethane diphosphonic acid;
O-(2-pyrimidyl)-2-oxa-ethane-1,1-diphosphonic acid;
O-(2-(3-picolyl))-2-oxa-ethane-1,1-diphosphonic acid;
O-(2-(3-picolyl))-oxamethane-diphosphonic acid;
O-(2-pyridyl)-1-hydroxy-2-oxa-ethane-1,1-diphosphonic acid;
O-(4-pyridyl)-1-amino-2-oxa-ethane-1,1-diphosphonic acid; and pharmaceutically-acceptable salts and esters thereof.

Preferred compounds are
N-(2-(5-amino)-pyridyl)-aminomethane diphosphonic acid;
N-(2-(5-chloro)-pyridyl)-aminomethane diphosphonic acid;
N-(2-(3-picolyl))-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-pyrimidyl)-aminomethane diphosphonic acid;
N-(2-pyridyl)-2-aminoethane-1,1-diphosphonic acid;
2-(2-pyridyl)-ethane-1,1-diphosphonic acid;
2-(3-pyridyl)-ethane-1,1-diphosphonic acid;
2-(4-pyridyl)-ethane-1,1-diphosphonic acid;
2-(2-pyridyl)-1-hydroxy-ethane-1,1-diphosphonic acid;
2-(3-pyridyl)-1-hydroxy-ethane-1,1-diphosphonic acid;
2-(4-pyridyl)-1-hydroxy-ethane-1,1-diphosphonic acid;
O-(2-(3-picolyl))-oxamethane-diphosphonic acid; and pharmaceutically-acceptable salts and esters thereof.

The diphosphonate compounds to be included in the pharmaceutical compositions of the present invention can be made using the synthetic methods disclosed in Japanese Patent 80-98,193 (Jul. 25, 1980, to Nissan Kygaku Kagyo K.K.), Japanese Patent 80-98,105 (Jul. 25, 1980, to Nissan Chemical Industries), West German Patent 2,831,578 (Feb. 1, 1979, to Fumio), and W. Ploger et al., Z. Anorg. Allg. Chem., 389, 119 (1972), the disclosures of which are incorporated herein by reference. The aminoethane diphosphonic acid compounds, however, are best prepared as follows:
Synthesis of N-(2-(3-picolyl))aminoethane DP The above-named compound is prepared via a typical Michael reaction between tetraethyl vinyldiphosphonate and 2-amino-3-picoline. (See H. O. House, Modern Synthetic Reaction 2nd Ed. W. A. Benjamin Inc. p. 595–623, the disclosure of which is incorporated herein by reference.)

To a solution of 1.62 g (15 mmol) of 2-amino-3-picoline in tetrahydrofuran at 5° C. was added 4.50 g (15 mmol) tetraethyl vinyldiphosphonate. The reaction mixture was stirred at room temperature for 16 hours. Evaporation of the solvent and chromatography (acetone/hexane, 4/1) of the product on silica gel gave pure tetraethyl N-(2-(3-picolyl))-2-aminoethane diphosphonate. P-31 NMR of the pure tetraethyl ester in CDCl$_3$ shows a resonance at 22.1 ppm. The ester was hydrolyzed in refluxing 6N HCl overnight. The product showed a P-31 NMR signal in D$_2$O at pH=12 of 19.0 ppm.

N-(2-pyridyl)-2-aminoethane DP and N-(2-(5-picolyl))-2-aminoethane DP were prepared in an identical manner.

Compounds having the general formula

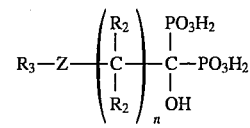

(wherein n is an integer of from 1 to about 5, preferably n=1; and Z, R$_2$ and R$_3$ are as described hereinbefore, with preferred Z being pyrimidine and especially pyridine, preferred R$_2$ being hydrogen, and preferred R$_3$ being one or more substituents selected from the group consisting of hydrogen, methyl, amino, chloro, nitro, methoxy, hydroxy, and combinations thereof) are best prepared as follows:
Synthesis of 2-(2-pyridyl)-1-hydroxy-ethane-1,1-diphosphonic acid A 3-neck round-bottom flask fitted with a reflux condenser and a magnetic stir bar is charged with 6.94 grams (0.04 mole) 2-pyridine acetic acid, 9.84 grams (0.14 mole) phosphorus acid, and 150 ml of chlorobenzene. This reaction mixture is heated on a boiling water bath, and 16.5 grams (0.12 mole) phosphorus trichloride is added dropwise with stirring. This reaction mixture is heated for 2½ hours during which time a viscous yellow oil forms. The reaction mixture is then cooled in an ice bath and the chlorobenzene solution is decanted off from the solidified product. The reaction flask containing this solidified product is charged with 150 ml of water and heated in a boiling water bath for several hours. The hot solution is then filtered through Celite 545®. 300 ml of methanol is added to the warm filtrate solution, and a precipitate develops. After cooling in ice for 1 hour, the precipitate is filtered off and then washed with methanol/water (1/1 volume/volume), methanol, and ether, and air dried. The product may be recrystallized from hot water. Yield is approximately 5.9 grams (52%). The sample is characterized by P-31 and C-13 NMR.

By "pharmaceutically-acceptable salts and esters" as used herein is meant hydrolyzable esters and salts of the diphosphonate compounds which have the same general pharmacological properties as the acid form from which they are derived, and which are acceptable from a toxicity viewpoint. Pharmaceutically-acceptable salts include alkali metal (sodium and potassium), alkaline earth metal (calcium and magnesium), non-toxic heavy metal (stannous and indium), and ammonium and low molecular weight substituted ammonium (mono-, di- and triethanolamine) salts. Preferred compounds are the sodium, potassium, and ammonium salts.

By "pharmaceutical carrier" as used herein is meant one or more compatible solid or liquid filler diluents or encapsulating substances. By "compatible" as used herein is meant that the components of the composition are capable of being commingled without interacting in a manner which would substantially decrease the pharmaceutical efficacy of the total composition under ordinary use situations.

Some examples of substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin, talc; stearic acid; magnesium stearate; calcium sulfate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents, lubricants, excipients, tableting agents, stabilizers, anti-oxidants and preservatives, can also be present. Other compatible pharmaceutical additives and actives (e.g., vitamin D or vitamin D metabolites, and mineral supplements) may be included in the pharmaceutical compositions of the present invention.

The choice of a pharmaceutical carrier to be used in conjunction with the diphosphonates of the present compositions is basically determined by the way the diphosphonate is to be administered. If the compound is to be injected, the preferred pharmaceutical carrier is sterile, physiological saline, the pH of which has been adjusted to about 7.4. However, the preferred mode of administering the diphosphonates of the present invention is orally, and the preferred unit dosage form is therefore tablets, capsules and the like, comprising from about 0.1 mg P to about 600 mg P of the diphosphonic acid compounds described herein. Pharmaceutical carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art. The pharmaceutical carrier employed in conjunction with the diphosphonates of the present invention is used at a concentration sufficient to provide a practical size to dosage relationship. Preferably, the pharmaceutical carrier comprises from about 0.01% to about 99.99% by weight of the total composition.

EXAMPLE I

Capsules are prepared by conventional methods, comprised as follows:

| Ingredient | Mg per capsule |
| --- | --- |
| N-(2-(3-picolyl)) AMDP | 100 (as mg P) |
| Starch | 55.60 |
| Sodium lauryl sulfate | 2.90 |

The above capsules administered orally twice daily for 6 months substantially reduce bone resorption in a patient weighing approximately 70 kilograms afflicted with osteoporosis. Similar results are obtained when the N-(2-(3-picolyl))-aminomethane diphosphonic acid, or its pharmaceutically-acceptable salt or ester, in the above-described capsules is replaced with
N-(2-(5-amino)-pyridyl)-aminomethane diphosphonic acid;
N-(2-(5-chloro)-pyridyl)-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-pyrimidyl)-aminomethane diphosphonic acid;
N-(2-pyridyl)-2-aminoethane-1,1-diphosphonic acid;
2-(2-pyridyl)-ethane-1,1-diphosphonic acid;
2-(3-pyridyl)-ethane-1,1-diphosphonic acid;
2-(4-pyridyl)-ethane-1,1-diphosphonic acid;
2-(2-pyridyl)-1-hydroxy-ethane-1,1-diphosphonic acid;
2-(3-pyridyl)-1-hydroxy-ethane-1,1-diphosphonic acid;
2-(4-pyridyl)-1-hydroxy-ethane-1,1-diphosphonic acid;
O-(2-(3-picolyl))-oxamethane-diphosphonic acid; or the pharmaceutically-acceptable salts or esters thereof.

EXAMPLE II

Tablets are prepared by conventional methods, formulated as follows:

| Ingredient | mg per tablet |
| --- | --- |
| N-(2-pyrimidyl) AMDP | 25.00 |
| Lactose | 40.00 |
| Starch | 2.50 |
| Magnesium stearate | 1.00 |

The above tablets administered orally twice daily for 6 months substantially reduce bone resorption in a patient weighing approximately 70 kilograms afflicted with osteoporosis. Similar results are obtained when the N-(2-pyrimidyl) AMDP, or its pharmaceutically-acceptable salt or ester, in the above-described tablets is replaced with
N-(2-(5-amino)-pyridyl)-aminomethane diphosphonic acid;
N-(2-(5-chloro)-pyridyl)-aminomethane diphosphonic acid;
N-(2-(3-picolyl))-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-pyridyl)-2-aminoethane-1,1-diphosphonic acid;
2-(2-pyridyl)-ethane-1,1-diphosphonic acid;
2-(3-pyridyl)-ethane-1,1-diphosphonic acid;
2-(4-pyridyl)-ethane-1,1-diphosphonic acid;
2-(2-pyridyl)-1-hydroxy-ethane-1,1-diphosphonic acid;
2-(3-pyridyl)-1-hydroxy-ethane-1,1-diphosphonic acid;
2-(4-pyridyl)-1-hydroxy-ethane-1,1-diphosphonic acid;
O-(2-(3-picolyl))-oxamethane-diphosphonic acid; or the pharmaceutically-acceptable salts or esters thereof.

EXAMPLE III

Injectable solutions are prepared by conventional methods using 1.0 ml of either physiological saline or water solution and 3.5 mg of 2-(2-pyridyl)-ethane-1,1-diphosphonic acid, adjusted to pH=7.4.

One injection, one time daily for 4 days results in appreciable alleviation of hypercalcemia of malignancy in patients weighing approximately 70 kilograms.

Similar results are obtained when the 2-(2-pyridyl)-ethane-1,1diphosphonic acid in the above-described treatment is replaced with
N-(2-(5-amino)-pyridyl)-aminomethane diphosphonic acid;
N-(2-(5-chloro)-pyridyl)-aminomethane diphosphonic acid;
N-(2-(3-picolyl))-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-pyrimidyl)-aminomethane diphosphonic acid;
N-(2-pyridyl)-2-aminoethane-1,1-diphosphonic acid;
2-(3-pyridyl)-ethane-1,1-diphosphonic acid;
2-(4-pyridyl)-ethane-1,1-diphosphonic acid;
2-(2-pyridyl)-1-hydroxy-ethane-1,1-diphosphonic acid;
2-(3-pyridyl)-1-hydroxy-ethane-1,1-diphosphonic acid;
2-(4-pyridyl)-1-hydroxy-ethane-1,1-diphosphonic acid;
O-(2-(3-picolyl))-oxamethane-diphosphonic acid; or pharmaceutically-acceptable salts or esters thereof.

The compositions of the present invention are useful in the treatment of abnormal calcium and phosphate metabolism. Other diphosphonic acids and their pharmaceutically-acceptable salts have been proposed for use in the treatment and prophylaxis of such conditions. In particular, ethane-1-hydroxy-1,1-diphosphonic acid (EHDP), propane-3-amino- 1-hydroxy-1,1-diphosphonic acid (APD), and dichloromethane diphosphonic acid ($Cl_2MDP$) have been the subject of considerable research efforts in this area.

However, the compositions of the present invention are generally more biologically potent in inhibiting bone resorption than the art-disclosed diphosphonates. Thus, the compositions of the present invention may provide one or more of the following advantages over the art-disclosed diphosphonates of (1) being more potent in inhibiting bone resorption; (2) possessing less potential for inhibition of bone mineralization, since mineralization inhibition is believed to be predominantly a mass related physico-chemical effect; (3) having generally a wider margin of safety (i.e., wider dosing interval between the lowest effective antiresorptive dose and the lowest dose producing mineralization inhibition); (4) allowing lower oral dosages to be administered, thereby avoiding the gastro-intestinal discomfort (like diarrhea) sometimes associated with higher dosages of diphosphonates; and (5) having potential for flexibility of dosing methods.

Another aspect of this invention is a method for treating or preventing diseases characterized by abnormal calcium and phosphate metabolism, in particular those which are characterized by abnormal bone metabolism, in persons at risk to such disease, comprising the step of administering to persons in need of such treatment a safe and effective amount of a diphosphonic acid-containing composition of the present invention.

The preferred mode of administration is oral, but other modes of administration include, without limitation, transdermal, mucosal, sublingual, intramuscular, intravenous, intraperitoneal, and subcutaneous administration, as well as topical application.

By "abnormal calcium and phosphate metabolism" as used herein is meant (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Pagets disease, hyperparathyroidism, hypercalcemia of malignancy, and osteolytic bone metastases. The second category includes, but is not limited to, myositis ossificans progressiva, calcinosis universalis, and such afflictions as arthritis, neuritis, bursitis, tendonitis and other inflammatory conditions which predispose involved tissue to deposition of calcium phosphates.

By "person at risk", or "person in need of such treatment", as used herein is meant any human or lower animal which suffers a significant risk of abnormal calcium and phosphate metabolism if left untreated, and any human or lower animal diagnosed as being afflicted with abnormal calcium and phosphate metabolism. For example, postmenopausal women; persons undergoing certain steroid therapy; persons on certain anti-convulsant drugs; persons diagnosed as having Pagets disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., postmenopausal women, men over age 65, and persons being treated with drugs known to cause osteoporosis as a side effect; persons diagnosed as suffering from myositis ossificans progressiva or calcinosis universalis; and persons afflicted with arthritis, neuritis, bursitis, tendonitis and other inflammatory conditions which predispose involved tissue to diposition of calcium phosphate.

By "human or lower animal afflicted with or at risk to osteoporosis" as used herein is meant a subject diagnosed as suffering from one or more of the various forms of osteoporosis, or a subject belonging to a group known to have a significantly higher than average chance of developing osteoporosis, e.g., postmenopausal women, men over the age of 65, and persons being treated with drugs known to cause osteoporosis as a side effect (such as adrenocorticoid).

By "safe and effective amount" as used herein is meant an amount of a compound or composition high enough to significantly positively modify the condition to be treated, but low enough to avoid serious side effects (at a reasonable benefit/risk ratio), within the scope of sound medical judgment. The safe and effective amount of diphosphonates will vary with the particular condition being treated, the age and physical condition of the patient being treated, the severity of the condition, the duration of treatment, the nature of concurrent therapy, and the specific diphosphonate employed. However, single dosages can range from about 0.001 mg P to about 3500 mg P, or from about 0.1 micrograms P/kg of body weight to about 500 mg P/kg of body weight. Preferred single dosages are from about 0.1 mg P to about 600 mg P, or from about 0.01 to about 50 mg P/kg of body weight. Up to about four single dosages per day may be administered. Daily dosages greater than about 2000 mg P/kg are not required to produce the desired effect and may produce undesirable side effects. The higher dosages within this range are, of course, required in the case of oral administration because of limited absorption.

Schenk Model

The compounds were evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87–99 (1983); and in Schenk et al., *Calcif. Tissue Res.* 11, 196–214 (1973), the disclosures of which are incorporated herein by reference.

Materials and Methods

Animals

Preweaning 17-day-old (30 gms) male Sprague Dawley rats (Charles River Breeding Laboratories) were shipped with their mothers and placed in plastic cages with their mothers upon arrival. At 21 days of age, pups receiving Rat Chow and water ad libitum were randomly allocated into treatment groups comprising five animals per group, except for control animals receiving saline vehicle which had 10 rats per group. On day 0 and again on day 1 all animals were given a subcutaneous injection of Calcein (Sigma) as a 1% solution in 0.9% NaCl solution to label the skeleton.

Dose Solutions and Dosing Procedure

All solutions were prepared for subcutaneous injection in 0.9% normal saline and adjusted to pH 7.4 using NaOH and/or HCl. Dose solution calculation was made by considering the mass of powder (based on molecular weight, hydration) of the active material in mg/kg (body weight) that corresponds to mgP/kg. Concentrations were based on dosing 0.2 ml/100 g body weight. Initially, all compounds were administered at 0.1, 1.0 and 10.0 mg P/kg/day for 7 days. Compounds showing activity at 0.1 mg P/kg/day were then tested at logarithmic decrements down to 0.001 mg P/kg/day. Adjustments in dosage based on changes in body weight were made on a daily basis.

Necropsy, Tissue Processing and Histomorphometry

On day 8 after the start of dosing, all animals were sacrificed by $CO_2$ asphyxiation. Tibias were dissected free and placed in 70% ethyl alcohol. One tibia was dehydrated in graded ethanol solutions and embedded in methyl methacrylate using a rapid procedure described in Boyce et al., *Lab. Investig.*, 48, 683–689 (1983), the disclosures of which are incorporated herein by reference. The tibia was sectioned longitudinally through the metaphyseal area (Leitz® saw microtome at 150μ). Specimens were stained on one surface with silver nitrate and mounted on microscope slides for evaluation with a Quantimet Image Analyzer (Cambridge Instruments, Inc. ) using both incandescent and ultraviolet illumination. Metaphyseal trabecular bone content was measured in the region between the fluorescent label and the growth plate: expressed as percent of total area (bone+ marrow). Epiphyseal growth plate width was obtained as the mean value of 10 equally-spaced measurements across the section.

Statistical evaluation of data was made using parametric and non-parametric analysis of variance and Wilcoxons rank sum test to determine a statistically significant effect compared to control animals.

The Schenk model provided data for in vivo bone resorption inhibition by the compounds. The lowest effective (antiresorptive) dose ("LED") for representative compounds tested, as determined by the Schenk model, are provided in Table I.

TABLE I

Lowest Effective (Antiresorptive) Dose

| Diphosphonate Compound | Schenk LED (mg P/kg) |
| --- | --- |
| EHDP | 1.0 |
| $Cl_2$MDP | 1.0 |
| APD | 0.1 |
| N-(2-pyridyl) AMDP* | 0.01 |
| N-(2-(5-chloro)-pyridyl) AMDP* | 0.01 |
| N-(2-(3-picolyl)) AMDP* | 0.001 |
| N-(2-(4-picolyl)) AMDP* | 0.001 |
| N-(2-(5-picolyl)) AMDP* | 0.001 |
| N-(2-(6-picolyl)) AMDP* | 0.001 |
| N-(2-pyrimidyl) AMDP* | 0.001 |
| N-(4-pyridyl)-N-ethyl AMDP* | 0.1 |
| 2-(2-pyridyl) EDP* | 0.01 |
| 2-(3-pyridyl) EDP* | 0.01 |
| 1-(2-pyridyl) propyl DP* | 10 |

EHDP = ethane-1-1hydroxy-1,1-DP
$Cl_2$MDP = dichloromethane DP
APD = 3-aminopropane-1-hydroxy-1,1-DP
AMDP = aminomethane diphosphonic acid, where the ring is attached to the amine.
* = Compounds included in pharmaceutical compositions of the present invention.
EDP = ethane-1,1-diphosphonic acid, where the ring is attached at the 2 position of the ethane.
Propyl DP = propane-2,2-diphosphonic acid Diphosphonate compounds which have a bone mineralization inhibiting effect cause widening of the epiphyseal growth plate, since matrix production continues but mineralization is impeded. The widening of the epiphyseal growth plate as observed in the Schenk model is, therefore, a measure of the mineralization inhibiting effect of the diphosphonate compound tested.

The lowest tested dosages producing a statistically significant widening of epiphyseal growth plate for compounds tested are given in Table II.

TABLE II

Mineralization Inhibition (Schenk Model))

| Diphosphonate Compound | Lowest tested dosage producing a statistically significant widening of epiphyseal growth plate (mg P/Kg) |
| --- | --- |
| EHDP | 10 |
| APD | 10 |
| $Cl_2$MDP | — |
| N-(2-pyridyl) AMDP* | 0.1 |
| N-(4-pyridyl)-N-ethyl AMDP* | —[1] |
| N-(2-(3-picolyl)) AMDP* | —[1] |
| N-(2-(4-picolyl)) AMDP* | 0.1 |
| N-(2-(5-picolyl)) AMDP* | 0.1 |
| N-(2-(6-picolyl)) AMDP* | —[1] |
| N-(2-pyrimidyl) AMDP* | 1.0 |
| N-(2-(5-chloro)-pyridyl) AMDP* | —[1] |
| 2-(3-pyridyl) EDP* | — |
| 2-(2-pyridyl) EDP* | —[1] |

— = No plate widening observed at highest dose tested (highest dose tested is 10 mg P/kg/day unless otherwise indicated)
[1] = Highest dose evaluated is 1 mg P/kg/day (compound lethally toxic at 10 mg P/kg/day)
EHDP = ethane-1-hydroxy-1,1-DP
APD = 3-aminopropane-1-hydroxy-1,1-DP
$Cl_2$MDP = Dichloromethane DP
AMDP = aminomethane diphosphonic acid, where the ring is attached to the amine
EDP = ethane-1,1-diphosphonic acid, where the ring is attached at the 2 position of the ethane
* = Compounds included in pharmaceutical compositions of the present invention Thyroparathyroidectomized (TPTX) Rat Model The compounds were evaluated for in vivo bone resorption inhibition potency by an animal model system known as the thyroparathyroidectomized (TPTX) rat model. The general principles of this model system are disclosed in Russell et al., *Calcif. Tissue Research*, 6, 183–196 (1970), and in Muhlbauer and Fleisch, *Mineral Electrolyte Metab.*, 5, 296–303 (1981), the disclosures of which are incorporated herein by reference. The basic biochemical concept of the TPTX system is inhibition of the parathyroid hormone (PTH)—induced rise in serum and ionized calcium levels by the respective bone active polyphosphonates.

Materials and Methods

Materials

Low calcium and low phosphorous diets used were prepared by Teklad® Test Diets (Harlan Industries, Madison, Wis. 53711; Order #TD82195) in a pellet form of approximately 0.18% calcium and 0.22% phosphorous. The diets contained all the essential vitamins and minerals required for the rat, with the exception of calcium and phosphorous. The calcium and phosphorous levels of the pellets were verified analytically (Procter & Gamble Co., Miami Valley Laboratories, Cincinnati, Ohio).

PTH was acquired as a powdered bovine extract (Sigma Chemical Co., P. O. Box 14508, St. Louis, Mo., order #P-0892, Lot #72F-9650) at an activity of 138 USP units per mg. PTH was prepared in 0.9% saline such that the final concentration was 100 U.S.P./ml. All solutions were filtered through a #4 Whatman Filter Paper and refiltered through a 0.45 μm Metricel® filter.

Dose solutions and Dosing Procedure

All solutions of compounds to be tested for bone resorption inhibition potency were prepared for subcutaneous injection in 0.9% normal saline and adjusted to pH 7.4 using NaOH and/or HCl. Dose solution calculation was made by considering the mass of powder (based on molecular weight, hydration) of the active material in mg/kg (body weight) that corresponds to mg P/kg. Concentrations were based on dosing 0.2 ml/100 grams of body weight. Initially, all compounds were administered at 0.01, 0.1, and 1.0 mg P/kg/day for 4 days. Where necessary the test was repeated, whereby the animals were administered with 0.5 LED in order to refine the determination of LED. Adjustments in dosage based on changes in body weight were made on a daily basis.

Animals

In this study 50 male Wistar rats weighing approximately 150–160 grams were thyroparathyroidectomized surgically by the breeder (Charles River Breeding Laboratories). All rats were double housed on arrival in suspended cages with Purina Laboratory Rodent Chow® and tap water ad libitum. After acclimation to the laboratory environment for 3–5 days, the rats were placed on a low calcium, low phosphorous (0.18%/0.22%) diet (Teklad®) and given 2% (W/V) calcium gluconate supplemented deionized water via water bottles.

Method

On day four of low-calcium diet all rats were anesthetized with Ketaset® (Ketamine Hydrochloride, 100 mg/ml, Bristol Myers), 0.10 ml/100 grams of body weight, weighed and then bled from the retro-orbital venous plexus for serum total calcium analysis using Flame Atomic Absorption (FAA). All rats weighing less than 180 grams were eliminated from the study. Animals were then randomized statistically such that the mean total serum calcium for each group was the same. Only rats deemed hypocalcemic (total serum calcium≦8.0 mg/dl) were placed in study groups comprising six animals per group.

Treatments with the various experimental compounds commenced on day 6 and lasted through day 9 of the study (at 1:00 P.M. each day). Dose solutions were prepared to be given at a constant rate of 0.2 ml/100 grams of body weight subcutaneously in the ventral skin flap where the hind leg meets the torso. All rats were weighed and dosed daily. A 25 gauge ⅝" needle was used to administer drug, alternating dose sites daily. On day 8, animals were changed to deionized, distilled water via water bottles. On day 9 all rats were fasted in the afternoon at approximately 4:00 P.M. On day 10 of study no treatment was given. In the morning a 600 μl sample of whole blood was collected from each rat in Microtainer (B-D#5060) serum separater tubes for serum total calcium (FAA). Two 125 μl samples of heparinized whole blood were also collected to be used for ionized calcium analysis. Immediately following blood collection all rats were weighed and injected with bovine parathyroid hormone subcutaneously at a rate of 75 USP (filtered) per 100 grams of body weight. Blood sampling for total and ionized calcium was repeated three and one-half hours post-PTH injection.

All pre- and post-PTH total and ionized calciums were statistically analyzed for significance compared to PTH alone (control) using Students t-test, analysis of variance, and their non-parametric equivalents. The post minus pre-change and % change were also determined on calcium levels and pre-drug vs post-drug body weights.

The physiological effect of the PTH challenge is a rise in serum calcium level, with peak activity observed at three and one-half hours. Since the hormonal and dietary controls of calcium metabolism are minimized in the TPTX model, an observed increase in serum calcium level is presumably the result of resorption of bone material. Since polyphosphonates tend to inhibit resorption of bone materials, the animals pretreated with polyphosphonate showed a rise in serum calcium level after PTH challenge which was less than that found in control animals which had been treated with saline vehicle instead. The lowest dose at which the polyphosphonate is capable of inhibiting bone resorption, as evidenced by a decreased rise in serum calcium upon PTH challenge, is a measure of the bone resorption inhibition potency of the polyphosphonate. The LED values of the bone resorption inhibition potency of representative compounds as determined by the TPTX rat model are presented in Table III.

TABLE III

| Lowest Effective (Antiresorptive) Dose | |
|---|---|
| Diphosphonate Compound | TPTX LED (mg P/kg) |
| EHDP | 1.0 |
| Cl$_2$MDP | 1.0 |
| APD | 0.1 |
| N-(2-pyridyl) AMDP* | 0.01 |
| N-(2-(5-amino)-pyridyl) AMDP* | 0.01 |
| N-(2-(5-chloro)-pyridyl) AMDP* | 0.01 |
| N-(2-(5-nitro)-pyridyl) AMDP* | 0.1 |
| N-(2-(5-carboxy)-pyridyl) AMDP | N |
| N-(2-(3,5-dichloro)-pyridyl) AMDP* | 1.0 |
| N-(4-pyridyl)-N-ethyl AMDP* | 0.1 |
| N-(2-(3-picolyl)) AMDP* | 0.002 |
| N-(2-(4-picolyl)) AMDP* | 0.001 |
| N-(2-(5-picolyl)) AMDP* | 0.001 |
| N-(2-(6-picolyl)) AMDP* | 0.01 |
| N-(2-(3,4-lutidine)) AMDP* | 0.01 |
| N-(2-(4,6-lutidine) AMDP* | 0.01[1)] |
| N-(2-pyrimidyl) AMDP* | 0.01 |
| N-(4-(2,6-dimethyl)-pyrimidyl) AMDP* | 1.0 |
| N-(2-(4,6-dihydroxy)-pyrimidyl) AMDP* | 0.01[1)] |
| N-(2-pyridyl) AEDP* | 0.01 |
| N-(2-(3-picolyl) AEDP* | 10 |
| 2-(2-pyridyl) EDP* | 0.01 |
| 2-(3-pyridyl) EDP* | 0.01 |
| 2-(4-pyridyl) EDP* | 0.1 |
| 1-(2-pyridyl) propyl DP* | 1.0 |
| 2-(2-pyridyl)-1-chloroethane DP* | 0.1 |
| O-(2-pyridyl)-oxamethane DP* | 1.0 |
| O-(2-(3-picolyl))-oxamethane DP* | 0.1 |

N = no activity at any of the dosage levels tested
EHDP = ethane-1-hydroxy-1,1-DP
Cl$_2$MDP = dichloromethane DP
APD = 3-aminopropane-1-hydroxy-1,1-DP
AMDP = aminomethane diphosphonic acid, where the ring is attached to the amine
AEDP = 2-aminoethane-1,1-diphosphonic acid, where the ring is attached to the amine
EDP = ethane-1,1-diphosphonic acid, where the ring is attached at the 2 position of the ethane
propyl DP = propane-2,2-diphosphonic acid
* = Compounds included in pharmaceutical compositions of the present invention
[1)] = activity level questionable due to lack of dose response

EXAMPLE IV

Patients weighing approximately 70 kilograms who are clinically diagnosed as suffering from hypercalcemia of malignancy are administered 0.7 mg P of 2-(2-pyridyl)-ethane-1,1-diphosphonic acid, or its pharmaceutically-acceptable salt or ester, by a 2½ hour intravenous infusion one time daily for 4 days. This treatment results in an appreciable alleviation of the hypercalcemia of malignancy.

Similar results are obtained when the 2-(2-pyridyl)-ethane-1,1-diphosphonic acid in the above-described treatment is replaced with
N-(2-(5-amino)-pyridyl)-aminomethane diphosphonic acid;

N-(2-(5-chloro)-pyridyl)-aminomethane diphosphonic acid;
N-(2-(3-picolyl))-aminomethane diphosphonic acid;
N-(2-(4-picolyl))-aminomethane diphosphonic acid;
N-(2-(5-picolyl))-aminomethane diphosphonic acid;
N-(2-(6-picolyl))-aminomethane diphosphonic acid;
N-(2-(3,4-lutidine))-aminomethane diphosphonic acid;
N-(2-pyrimidyl)-aminomethane diphosphonic acid;
N-(2-pyridyl)-2-aminoethane-1,1-diphosphonic acid;
2-(3-pyridyl)-ethane-1,1-diphosphonic acid;
2-(4-pyridyl)-ethane-1,1-diphosphonic acid;
2-(2-pyridyl)-1-hydroxy-ethane-1,1-diphosphonic acid;
2-(3-pyridyl)-1-hydroxy-ethane-1,1-diphosphonic acid;
2-(4-pyridyl)-1-hydroxy-ethane-1,1-diphosphonic acid;
O-(2-(3-picolyl))-oxamethane-diphosphonic acid; or pharmaceutically-acceptable salts or esters thereof.

What is claimed is:

1. A diphosphonic acid compound, or a pharmaceutically-acceptable salt or ester thereof, having the structure:

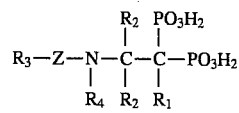

wherein Z is a pyridine ring; $R_1$ is hydrogen substituted or unsubstituted amino, amido, hydroxy, $C_1$–$C_6$ alkoxy, halogen, carboxylate, a substituted or unsubstituted, a saturated or unsaturated hydrocarbon chain having from 1 to 6 carbon atoms, substituted or unsubstituted phenyl, or substituted or unsubstituted benzyl; $R_2$ is hydrogen, or a substituted or unsubstituted, saturated or unsaturated hydrocarbon chain having from 1 to 4 carbon atoms; $R_3$ is hydrogen, a substituted or unsubstituted, saturated or unsaturated hydrocarbon chain having from 1 to 6 carbon atoms, substituted or unsubstituted benzyl, hydroxy, halogen, $C_1$–$C_6$ alkoxy, amino, substituted amino, substituted or unsubstituted phenyl, substituted or unsubstituted naphthyl, carbonyl, nitro, amido, or carboxylate; and $R_4$ is hydrogen, a substituted or unsubstituted, saturated or unsaturated hydrocarbon chain having from 1 to 4 carbon atoms, or acetyl; and wherein said substituted $R_1$, $R_2$, $R_3$ and $R_4$ groups are independently substituted with methyl, ethyl, amino, chloro, nitro, methoxy, hydroxy, acetamido, or acetate.

2. A diphosphonic acid compound, or a pharmaceutically-acceptable salt or ester thereof, having the structure:

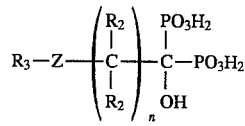

wherein Z is a pyridine ring; n is 0 or 1; $R_2$ is hydrogen, or a substituted or unsubstituted, saturated or unsaturated hydrocarbon chain having from 1 to 4 carbon atoms; and $R_3$ is hydrogen, a substituted or unsubstituted, saturated or unsaturated hydrocarbon chain having from 1 to 6 carbon atoms, substituted or unsubstituted benzyl, hydroxy, halogen, $C_1$–$C_6$ alkoxy, amino, substituted amino, substituted or unsubstituted phenyl, substituted or unsubstituted naphthyl, carbonyl, nitro, amido, or carboxylate; and wherein said substituted $R_2$ and $R_3$ groups are independently substituted with methyl, ethyl, amino, chloro, nitro, methoxy, hydroxy, acetamido, or acetate.

3. A diphosphonic acid compound, or a pharmaceutically-acceptable salt or ester thereof, having the structure:

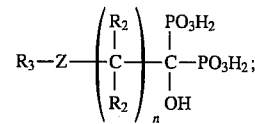

wherein Z is a pyridine ring n is 1; $R_2$ is hydrogen, or a substituted or unsubstituted, saturated or unsaturated hydrocarbon chain having from 1 to 4 carbon atoms; and $R_3$ is hydrogen, a substituted or unsubstituted, saturated or unsaturated hydrocarbon chain having from 1 to 6 carbon atoms, substituted or unsubstituted benzyl, hydroxy, halogen, $C_1$–$C_6$ alkoxy, amino, substituted amino, substituted or unsubstituted phenyl, substituted or unsubstituted naphthyl, carbonyl, nitro, amido, or carboxylate; and wherein said substituted $R_2$ and $R_3$ groups are independently substituted with methyl, ethyl, amino, chloro, nitro, methoxy, hydroxy, acetamido, or acetate.

4. A diphosphonic and acid compound, or pharmaceutically-acceptable salt or ester thereof, which is 2-(3-pyridyl)-1-hydroxyethane diphosphonic acid.

5. A pharmaceutical composition comprising:

(a) a geminal diphosphonic acid compound, or a pharmaceutically-acceptable salt or ester thereof, at a level providing from 0.001 to 600 mg of phosphorus in said composition, wherein said diphosphonic acid compound is of the formula:

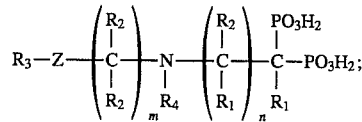

wherein Z is a pyridine ring; m+n is an integer from 0 to 5; $R_1$ is hydrogen, substituted or unsubstituted amino, amido, hydroxy, $C_1$–$C_6$ alkoxy, halogen, carboxylate, a substituted or unsubstituted, saturated or unsaturated hydrocarbon chain having from 1 to 6 carbon atoms, substituted or unsubstituted phenyl, or substituted or unsubstituted benzyl, except that when n=0, then $R_1$ is hydrogen, a substituted or unsubstituted, saturated or unsaturated hydrocarbon chain having from 1 to 6 carbon atoms, substituted or unsubstituted phenyl, or substituted or unsubstituted benzyl; $R_2$ is hydrogen, or a substituted or unsubstituted, saturated or unsaturated hydrocarbon chain having from 1 to 4 carbon atoms; $R_3$ is hydrogen, a substituted or unsubstituted, saturated or unsaturated hydrocarbon chain having from 1 to 6 carbon atoms, substituted or unsubstituted benzyl, hydroxy, halogen, $C_1$–$C_6$ alkoxy, amino, substituted amino, substituted or unsubstituted phenyl, substituted or unsubstituted naphthyl, carbonyl, nitro, amido, or carboxylate; and $R_4$ is hydrogen, a substituted or unsubstituted, saturated or unsaturated hydrocarbon chain having from 1 to 4 carbon atoms, or acetyl;

(b) a pharmaceutically-acceptable carrier.

6. A pharmaceutical composition comprising:

(a) a geminal diphosphonic acid compound, or a pharmaceutically-acceptable salt or ester thereof, at a level providing from 0.001 to 600 mg of phosphorus in said composition, wherein said diphosphonic acid compound is of the formula:

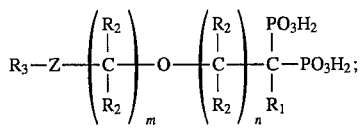

wherein Z is a pyridine ring; m+n is an integer from 0 to 5; $R_1$ is hydrogen, substituted or unsubstituted amino, amido, hydroxy, $C_1$–$C_6$ alkoxy, halogen, carboxylate, a substituted or unsubstituted, saturated or unsaturated hydrocarbon chain having from 1 to 6 carbon atoms, substituted or unsubstituted phenyl, or substituted or unsubstituted benzyl, except that when n=0, then $R_1$ is hydrogen, a substituted or unsubstituted, saturated or unsaturated hydrocarbon chain having from 1 to 6 carbon atoms, substituted or unsubstituted phenyl, or substituted or unsubstituted benzyl; $R_2$ is hydrogen, or a substituted or unsubstituted, saturated or unsaturated hydrocarbon chain having from 1 to 4 carbon atoms: and $R_3$ is hydrogen, a substituted or unsubstituted, saturated or unsaturated hydrocarbon chain having from 1 to 6 carbon atoms, substituted or unsubstituted benzyl, hydroxy, halogen, $C_1$–$C_6$ alkoxy, amino, substituted amino, substituted or unsubstituted phenyl, substituted or unsubstituted naphthyl, carbonyl, nitro, amido, or carboxylate; and (b) a pharmaceutically-acceptable carrier.

7. A pharmaceutical composition according to claim 5, wherein m+n=0.

8. A pharmaceutical composition according to claim 6, wherein m+n=0.

9. A pharmaceutical composition according to claim 7, wherein said diphosphonic acid compound is of the formula:

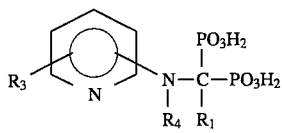

wherein $R_1$ is hydrogen; $R_3$ is hydrogen, methyl, amino, chloro, methoxy, nitro, or hydroxy; and $R_4$ is hydrogen, methyl, or ethyl.

10. A pharmaceutical composition according to claim 8, wherein said diphosphonic acid compound is of the formula:

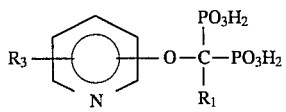

wherein $R_1$ is hydrogen, and $R_3$ is hydrogen, methyl, amino, chloro, methoxy, nitro, or hydroxy.

11. A pharmaceutical composition comprising:

(a) a geminal diphosphonic acid compound or a pharmaceutically-acceptable salt or ester thereof, at a level providing from 0.001 to 600 milligrams phosphorus in said composition, wherein said compound is of the formula:

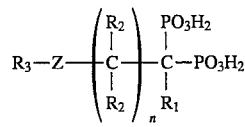

wherein Z is a pyridine ring; n is 0 or 1; $R_1$ is hydrogen, substituted or unsubstituted amino, amido, hydroxy, $C_1$–$C_6$ alkoxy, halogen, carboxylate, a substituted or unsubstituted, saturated or unsaturated hydrocarbon chain having from 1 to 6 carbon atoms, substituted or unsubstituted phenyl, or substituted or unsubstituted benzyl; $R_2$ is hydrogen, or a substituted or unsubstituted, saturated or unsaturated hydrocarbon chain having from 1 to 4 carbon atoms; and $R_3$ is hydrogen, a substituted or unsubstituted, saturated or unsaturated hydrocarbon chain having from 1 to 6 carbon atoms, substituted or unsubstituted benzyl, hydroxy, halogen, $C_1$–$C_6$ alkoxy, amino, substituted amino, substituted or unsubstituted phenyl, substituted or unsubstituted naphthyl, carbonyl, nitro, amido, or carboxylate; and wherein said substituted $R_1$, $R_2$ and $R_3$ groups are independently substituted with methyl, ethyl, amino, chloro, nitro, methoxy, hydroxy, acetamido, or acetate; and (b) a pharmaceutically-acceptable carrier.

12. A pharmaceutical composition according to claim 11, wherein n=1.

13. A pharmaceutical composition according to claim 11, wherein said diphosphonic acid compound is of the formula:

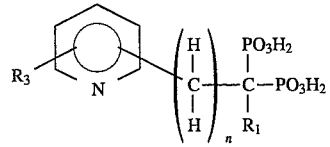

wherein n=0 or 1; $R_1$ is hydrogen, chloro, amino, or hydroxy; and $R_3$ is hydrogen, methyl, amino, chloro, methoxy, hydroxy, or nitro.

14. A pharmaceutical composition according to claim 12, wherein said diphosphonic acid compound is selected from the group consisting of 2-(2-pyridyl)-ethane-1,1-diphosphonic acid; 2-(3-pyridyl)-ethane-1,1-diphosphonic acid; 2-(4-pyridyl)-ethane-1,1-diphosphonic acid; 2-(2-pyridyl)-hydroxyethane-1,1-diphosphonic acid; 2-(3-pyridyl)-hydroxyethane-1,1-diphosphonic acid; and 2-(4-pyridyl)-hydroxyethane-1,1-diphosphonic acid.

15. A pharmaceutical composition according to claim 14, wherein said diphosphonic acid compound is 2-(2-pyridyl)-ethane-1,1-diphosphonic acid.

16. A pharmaceutical composition according to claim 14, wherein said diphosphonic acid compound is 2-(3-pyridyl)-hydroxyethane diphosphonic acid.

17. A method of treating diseases associated with abnormal calcium and phosphate metabolism, comprising administering to a person in need of such treatment a safe and effective amount of a composition of claim 5.

18. A method of treating diseases associated with abnormal calcium and phosphate metabolism, comprising administering to a person in need of such treatment a safe and effective amount of a composition of claim 6.

19. A method of treating diseases associated with abnormal calcium and phosphate metabolism, comprising administering to a person in need of such treatment a safe and effective amount of a composition of claim 7.

20. A method of treating diseases associated with abnormal calcium and phosphate metabolism, comprising administering to a person in need of such treatment a safe and effective amount of a composition of claim 12.

21. A method of treating diseases associated with abnormal calcium and phosphate metabolism, comprising administering to a person in need of such treatment a safe and effective amount of a composition of claim 14.

22. A method of treating diseases associated with abnormal calcium and phosphate metabolism, comprising administering to a person in need of such treatment a safe and effective amount of a composition of claim 15.

23. A method of treating diseases associated with abnormal calcium and phosphate metabolism, comprising administering to a person in need of such treatment a safe and effective amount of a composition of claim 16.

* * * * *

UNITED STATES PATENT AND TRADEMARK OFFICE
CERTIFICATE OF CORRECTION

| | | |
|---|---|---|
| PATENT NO. | : 5,583,122 | Page 1 of 1 |
| APPLICATION NO. | : 06/806155 | |
| DATED | : December 10, 1996 | |
| INVENTOR(S) | : Benedict, James J, and Perkins, Christopher M | |

It is certified that error appears in the above-identified patent and that said Letters Patent is hereby corrected as shown below:

Col. 18, line 22, please delete "and"

Signed and Sealed this

First Day of August, 2006

JON W. DUDAS
*Director of the United States Patent and Trademark Office*